United States Patent [19]

Evans et al.

[11] Patent Number: 4,945,923
[45] Date of Patent: Aug. 7, 1990

[54] CONTRACEPTIVE AND PROPHYLACTIC DEVICE

[76] Inventors: Mark I. Evans, 4734 Rolling Ridge, West Bloomfield, Mich. 48033; Frederick C. Greenwood, 949 Koae St., Honolulu, Hi. 96826

[21] Appl. No.: 378,449
[22] Filed: Jul. 10, 1989

Related U.S. Application Data

[63] Continuation of Ser. No. 89,970, Aug. 27, 1987, abandoned.

[51] Int. Cl.⁵ .................................................. A61F 6/00
[52] U.S. Cl. ........................................ 128/842; 128/79; 128/844; 128/918; 128/837; 604/347
[58] Field of Search .............................. 128/842–844, 128/79; 604/347–353, 329, 330

[56] References Cited

U.S. PATENT DOCUMENTS

| 32,566 | 4/1900 | Gagnier | 128/834 |
|---|---|---|---|
| 32,566 | 4/1900 | Gagnier | 128/127 |
| 733,068 | 7/1903 | Mitchell | 128/834 |
| 822,092 | 5/1906 | Woodruff | 604/352 |
| 1,634,555 | 7/1927 | Peloubet | 604/330 |
| 2,309,868 | 2/1943 | Robertson | 604/330 |
| 2,358,440 | 9/1944 | Bowman | 128/132 R |
| 2,410,460 | 11/1946 | Robinson | 604/93 |
| 2,915,065 | 12/1959 | Lyons | 604/329 |
| 3,037,508 | 6/1962 | Friedman | 128/127 |
| 3,128,762 | 4/1964 | Young | 128/127 |
| 3,130,721 | 4/1964 | Young | 128/837 |
| 3,536,066 | 11/1966 | Ludwig | 128/132 |
| 3,905,372 | 9/1975 | Denkinger | 128/834 |
| 4,388,923 | 6/1983 | Heimreid | 604/352 |
| 4,735,621 | 4/1988 | Hessel | 604/351 |
| 4,794,920 | 1/1989 | Robichaud | 128/844 |
| 4,840,624 | 6/1989 | Lee | 604/353 |

FOREIGN PATENT DOCUMENTS

| 0210413 | 5/1909 | Fed. Rep. of Germany | 604/328 |
|---|---|---|---|
| 0254211 | 11/1912 | Fed. Rep. of Germany | 604/349 |
| 0117234 | 10/1926 | Switzerland | 604/349 |
| 0275647 | 12/1986 | United Kingdom | 604/349 |

Primary Examiner—Mickey Yu
Assistant Examiner—Michael Brown
Attorney, Agent, or Firm—Bell, Seltzer, Park & Gibson

[57] ABSTRACT

A contraceptive device adapted to be worn by a female, and which serves to prevent the exchange of body fluids during intercourse, is disclosed. A preferred embodiment of the device has an elongate tubular sheath formed of thin, fluid impermeable material, the sheath having a closed inner end portion and an open outer end portion. A resilient inner ring is connected to the inner end portion for anchoring the same to the cervix of a wearer. An outer ring is connected to the open outer end portion for maintaining the outer end portion in an open configuration.

3 Claims, 1 Drawing Sheet

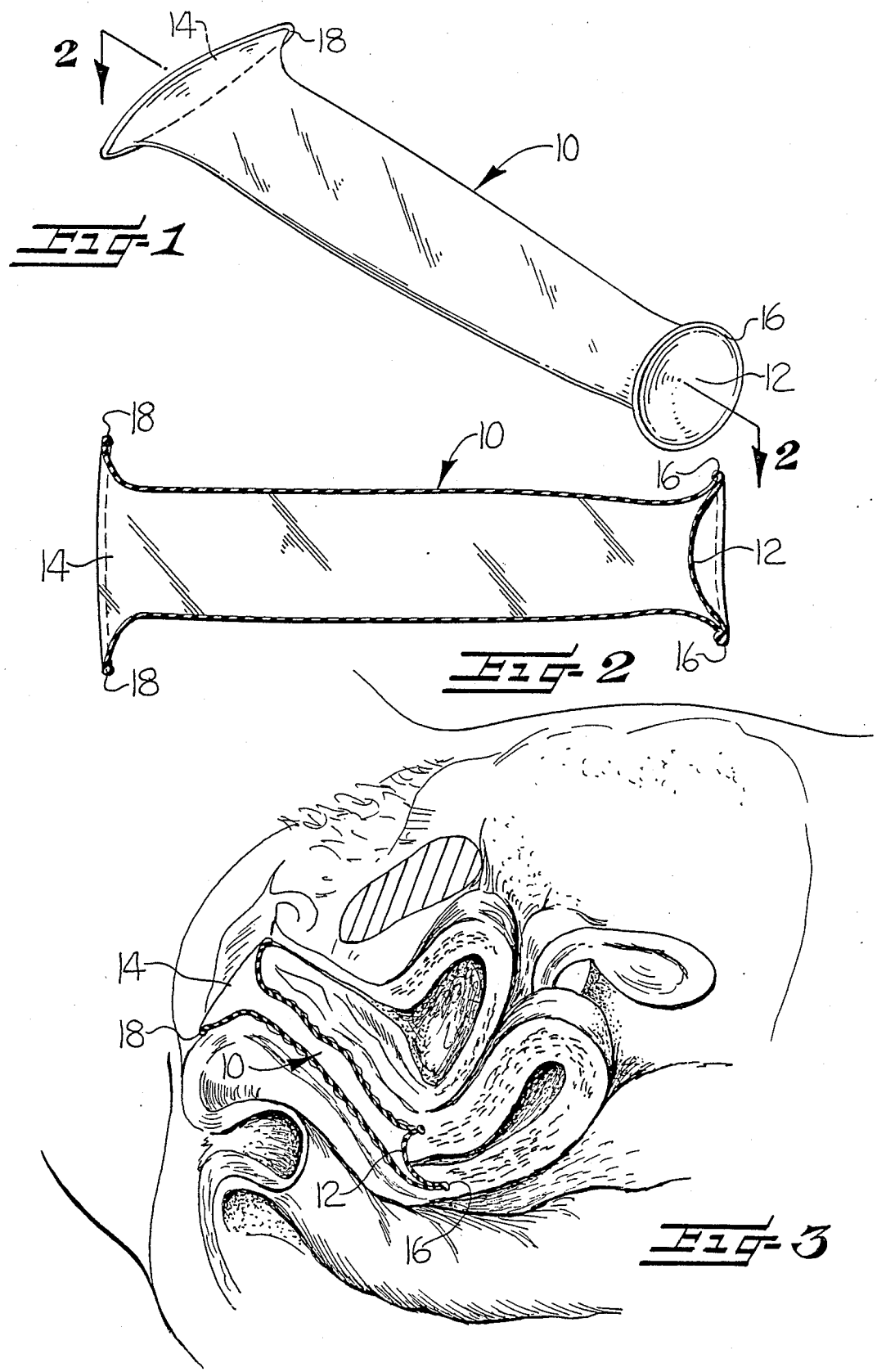

CONTRACEPTIVE AND PROPHYLACTIC DEVICE

This application is a continuation of application Ser. No. 089970 filed Aug. 27, 1987, now abandoned.

BACKGROUND OF THE INVENTION

Contraceptive devices which prevent the exchange of body fluids during sexual intercourse, and thereby serve as a prophylaxis against the sexual transmission of disease, have been known for many years. The best known of these devices is the conventional condom, though other devices in this general category have also been developed. See U.S. Pat. No. 2,410,460 to Robinson; U.S. Pat. No. 3,536,066 to Ludwig; and Swedish Patentschrift No. 117,234 to Liebermann.

With the staggering increase in sexually transmitted diseases such as AIDS, there has been a resurgence of interest in the use of prophylactic devices such as condoms. However, many men consider the use of condoms undesirable, and there is often great resistance to their use. The availability of a simple, convenient prophylactic device which could be worn by a woman would serve to reduce this problem by giving both sexual partners the option of using a device which will prevent the exchange of body fluids. Examination of such devices in the prior art, however, reveals them to be cumbersome. Insofar as this Applicant is aware, there is no contraceptive and prophylactic device adapted to be worn by a woman on the market today which serves to prevent the exchange of body fluids during sexual intercourse. An object of applicant's invention is to provide such a device.

SUMMARY OF THE INVENTION

The foregoing and other objects and advantages are achieved by a contraceptive device adapted to be worn by a female which serves to prevent the exchange of body fluids during intercourse, as disclosed herein. The device comprises an elongate tubular sheath formed of thin, fluid impermeable material, with the sheath having a closed inner end portion and an open outer end portion. A mounting means is connected to the closed inner end portion for anchoring the same so as to overlie the cervix of a wearer. Means are connected to the open outer end portion of the sheath for maintaining the outer end portion in an open configuration.

The foregoing device is described in detail in the following drawings and detailed description.

BRIEF DESCRIPTION OF THE DRAWINGS

FIG. 1 is a perspective view of a contraceptive device of the present invention.

FIG. 2 is a side sectional view of a contraceptive device of the present invention.

FIG. 3 is a side sectional view, in situ, of a contraceptive device of the present invention.

DETAILED DESCRIPTION OF THE PREFERRED EMBODIMENT

As shown in FIGS. 1 through 3, a contraceptive device of the present invention is comprised of an elongate tubular sheath 10 formed of thin, fluid impermeable material. The sheath has a closed inner end 12 and an open outer end 14. The sheath may be constructed of any suitable fluid impermeable material conventionally used in the construction of condoms and diaphragms, as known to those skilled in the art. Preferably the sheath is constructed of an elastic material such as latex.

A resilient inner ring 16 is connected to the inner end portion of the sheath, by a suitable adhesive or a heat seal. This ring is adapted to anchor the inner end of the sheath to the walls of the vagina surrounding the cervix of a wearer, in the manner illustrated in FIG. 3, and so that the sheath will not inadvertently fall out of the vaginal cavity. In the preferred embodiment, the resilient inner ring 16 and the closed inner end portion of the tubular sheath form a diaphragm-like cap which is anchored to the walls of the vagina in the manner of a conventional diaphragm used for birth control purposes. In this regard, it is contemplated that the contraceptive device of the present invention would be manufactured with rings 16 of different sizes, and that the proper size for a particular individual would be determined by a physical examination conducted by a physician, so as to insure a proper fit.

The resilient inner ring 16 may be constructed of the same materials used in the construction of rings employed in such conventional diaphragms, and as known to those skilled in the art. In addition, other forms of mounting means may also be used in practicing the present invention, an advantage of the invention being that it does not require the mounting means to form an absolute seal to insure that the exchange of body fluids is prevented since the tubular sheath itself serves as the fluid impermeable barrier, and not the mounting means. Exemplary of other suitable mounting means are those shown in U.S. Pat. No. 3,130,721 to Young, which discloses variations on a conventional diaphragm. Other forms of mounting means which provide a less perfect seal than those disclosed in the Young patent can also be used.

The device has an outer ring 18 connected to the outer end portion of the sheath to maintain the outer end portion in an open configuration. The outer ring 18 is preferably constructed of a resilient material, and may be constructed of the same material from which the inner ring is constructed. In most cases, the outer ring 18 has a circumference somewhat greater than that of the inner ring 16. In addition, the outer ring preferably has a generally oval configuration. The elongate tubular sheath 10 is sized and configured so that the outer ring 18 is adapted to be positioned exterior to and adjacent the vaginal introitus of a wearer. Thus, the fact that the inner end of the sheath is anchored to the cervix and the outer end is supported exterior to the vaginal introitus, serves to maintain the sheath in an extended, open configuration. This in turn prevents the sheath from gathering in a manner which could interfere with normal intercourse.

It is also understood that a lubricant may be used to facilitate normal intercourse within the device.

The invention has been disclosed with a degree of specificity above, with reference to a preferred embodiment. This disclosure has been provided for illustrative purposes only, and it will be understood that the present invention can be embodied in numerous different forms. Accordingly, the scope of this invention is defined by the following claims, with equivalents of the claims to be included therein.

That which is claimed is:

1. A contraceptive device adapted to be worn by a female which serves to prevent the exchange of body fluids during intercourse, comprising:

an elongate tubular sheath formed of thin, flexible, fluid impermeable material, said sheath having a closed inner end portion and an open outer end portion;

a resilient inner ring directly connected about the entire periphery thereof to said inner end portion of said tubular sheath for mounting said inner end portion to the walls of the vagina so as to overlie the cervix of a wearer, and such that no portion of said closed end of said sheath extends radially outwardly from said inner ring, and an outer ring directly connected about the entire periphery thereof to said open outer end portion for maintaining said outer end portion in an open configuration, said elongate tubular sheath and said outer ring being sized and configured so that said inner ring and said closed inner end portion may be mounted to overlie the cervix and with said outer ring positioned exterior to and adjacent the vaginal introitus of a wearer and so as to permit normal intercourse.

2. A contraceptive device as claimed in claim 1, wherein said outer ring is a resilient ring having a generally oval configuration.

3. A contraceptive device as claimed in claim 1 wherein said outer ring has a circumference greater than that of said inner ring.

* * * * *